United States Patent

Spencer, Jr. et al.

[11] Patent Number: 5,156,311
[45] Date of Patent: Oct. 20, 1992

[54] DENTAL FLOSS DISPENSER

[75] Inventors: John W. Spencer, Jr., Rising Sun, Md.; Edward F. John, Pottstown, Pa.

[73] Assignee: W. L. Gore & Associates, Inc., Newark, Del.

[21] Appl. No.: 840,736

[22] Filed: Feb. 21, 1992

[51] Int. Cl.$^5$ .............................. B26F 3/00
[52] U.S. Cl. ........................ 225/41; 225/47; 225/77; 206/389; 242/138
[58] Field of Search ............ 225/39, 41, 46, 47, 225/48, 77; 132/323, 324; D28/64; 242/138; 206/63.3, 389; 283/114

[56] References Cited

U.S. PATENT DOCUMENTS

| | | | |
|---|---|---|---|
| 876,866 | 1/1908 | Downing et al. | 225/41 X |
| 2,929,541 | 3/1960 | Castelli et al. | 225/51 |
| 3,246,815 | 4/1966 | Aronson | 225/44 |
| 3,480,190 | 11/1969 | Freedman | 225/33 |
| 4,162,688 | 7/1979 | Tarrson et al. | 132/92 A |
| 4,706,843 | 11/1987 | Thornton | 242/138 X |
| 4,884,734 | 12/1989 | Kahl, Jr. et al. | 225/46 X |
| 4,925,073 | 5/1990 | Tarrson et al. | 225/46 X |

Primary Examiner—Frank T. Yost
Assistant Examiner—Kenneth E. Peterson
Attorney, Agent, or Firm—Gary A. Samuels

[57] ABSTRACT

A dental floss dispenser comprising a molded unitary plastic housing composed of three main sections connected by two hinges which permits the dispenser to be easily opened and dental floss contained therein to be replaced by the user. A front section of the molded unitary plastic housing contains an opening and a molded post adjacent to the opening. A window assembly, molded of a transparent plastic, is engaged with the molded unitary plastic housing through placement of a hollow shaft having an axial bore capable of receiving the molded post over the molded post.

5 Claims, 3 Drawing Sheets

DENTAL FLOSS DISPENSER

FIELD OF THE INVENTION

The present invention is directed to a dental floss dispenser. More specifically, this invention is directed to a dental floss dispenser formed from a plastic material capable of being molded into a box-like body with integral hinge members and a second transparent plastic material which is capable of being molded into window and axle assembly for insertion into the box-like body.

BACKGROUND OF THE INVENTION

The advantages of dental floss have been well documented and dental floss has been widely sold and widely used. Dental floss has been typically available in dispensers which permit a user to dispense a desired length of floss while storing the remainder of the unused floss in a reasonably hygienic manner.

The choice of materials from which to fabricate dental floss dispensers are limited to those materials accepted by regulator agencies as being safe for the storage of such materials and by the cost of such materials. These dispensers are typically fabricated from one type of plastic which is opaque in nature. The choice of the plastic is usually determined by the ability of the plastic to be easily and economically molded into a shape. It is also desirable for the plastic to posses the ability to form an integral or "living" hinge thereby permitting molding of moveable parts from a single piece of plastic. However, plastics that possess the ability to form a "living" hinge are typically opaque in nature and therefore do not permit the user to view the interior of the dispenser offering no opportunity for the user to determine how much dental floss is present in the dispenser.

Transparent plastics have been used to fabricate dental floss dispensers. Dispensers fabricated from these materials permit one to view the contents of the dispenser without exposing its contents thereby keeping the unused portion of the dental floss in a reasonably hygienic state. However, the transparent materials typically do not offer the opportunity to include "living" hinges in the design of the dispenser and therefore preclude design of a dispenser with unitary hinges.

Dental floss dispensers have been designed which incorporate a body of opaque plastic capable of forming a living hinge and a window of a transparent material thereby permitting a user to determine how much dental floss remains within the dispenser. However, producing such a dispenser presents difficulties since the transparent material must be secured to the opaque material thereby requiring complex molds and/or skilled assembly.

Dental floss dispensers are usually quite durable and could function for an extended period of time, however, dental floss dispensers contain finite lengths of dental floss and a typical dental floss dispenser design does not provide the user with an opportunity to refill the dispenser with a fresh supply of dental floss when the supply contained within the dispenser is depleted. The dispenser is typically discarded.

The instant invention is directed to a novel dental floss dispenser which has a body of a plastic capable of forming a "living" hinge in which is secured a window of a transparent plastic. The dispenser permits a user to refill the dispenser with a new supply of floss thereby extending the useful life of the dispenser.

BRIEF DESCRIPTION OF THE INVENTION

A dental floss dispenser is disclosed comprising a molded unitary plastic housing engaged with a window assembly. The molded unitary plastic housing has a front section, a back section and a cover. A first hinge means is interposed between the front section and the back section, and a second hinge means is interposed between the back section and the cover thereby forming an enclosure for holding a filament spool. The front section is arranged with a front wall, having an opening, and a post on the inside having a keyed profile perpendicular to and adjacent to the opening, and a shoulder saddle perpendicular to the front wall and at the top having a guide for sliding a filament from the enclosure and a means for cutting the filament.

The window assembly has two faces. The first face being arranged with a transparent raised planar section that coincides with the opening of the front section, and a peripheral flange surrounding the transparent raised planar section; the second face is constructed with a column in alignment with the peripheral flange and projecting perpendicularly from the second face; the second face also constructed with a hollow shaft. The hollow shaft having a circular outside diameter for rotatably mounting the filament spool and an axial bore having an internal profile complementary to the post with a keyed profile. The shaft is in alignment with the peripheral flange and projects perpendicularly from the second face.

By positioning the transparent raised planar section within the opening in the front wall of the front section, and meshing the axial bore of the shaft with the post having a keyed profile, the window assembly is securely engaged with the molded unitary plastic housing assembly.

DETAILED DESCRIPTION OF THE INVENTION

Figure 1:
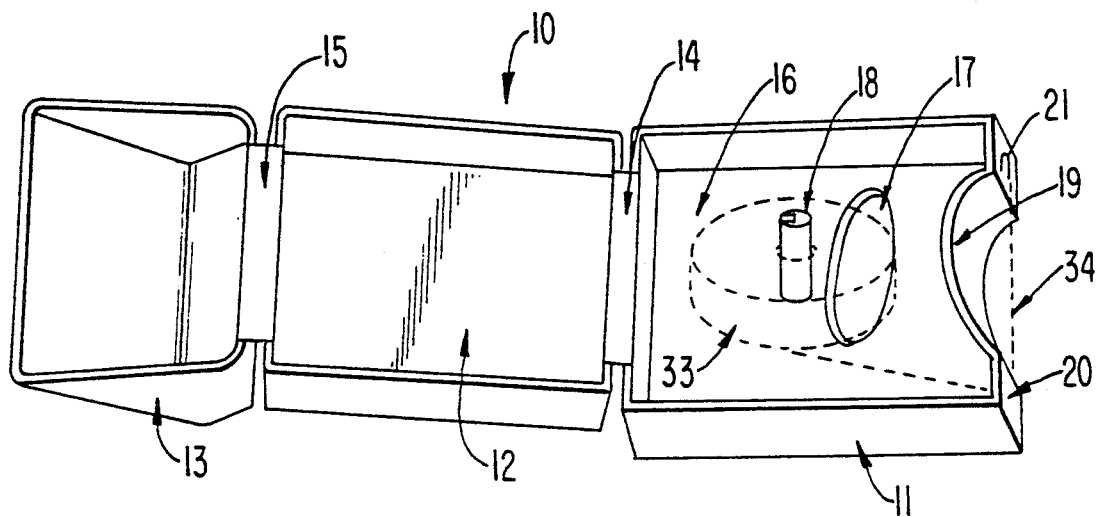
FIG. 1 is a perspective view of a unitary plastic housing of the inventive dental floss dispenser in which the hinges are in an open position to expose the entire interior of the dispenser.

A dental floss dispenser is disclosed comprising a molded unitary plastic housing engaged with a window assembly. Referring to FIG. 1, a molded unitary plastic housing 10 having a front section 11, a back section 12 and a cover 13 is depicted. The molded unitary plastic housing is formed through a molding process, preferably an injection molding process wherein a molten thermoplastic polymer is injected into a cavity of a mold thereby forming the molded unitary plastic housing. The molten thermoplastic polymer can be any thermoplastic polymer capable of producing a "living hinge" and accepted for use in dental floss dispensers by the Food and Drug Administration (FDA). The "living hinge" is a thin area in a molded plastic part which enables the molded plastic part to fold along a crease line thereby forming a hinge. Certain thermoplastic polymers are capable of producing these "living hinges". The preferred thermoplastic polymer in the instant invention is polypropylene.

Still referring to FIG. 1, a first hinge means 14 is interposed between the front section 11 and the back section 12. A second hinge means 15 is interposed between the back section 12 and the cover 13. When the front section 11 is folded along the first hinge means 14 towards the back section 12 while the back section is folded along the second the second hinge means 15, an enclosure for holding a filament spool is produced. To simplify assembly of the enclosure, it is preferable that both the first hinge means and the second hinge means are "living hinges" since both may be produced in a single molding step.

Still referring to FIG. 1, the front section 11 is arranged with a front wall 16 which has an opening 17 and a post 18 having a keyed profile. A shoulder saddle 19 perpendicular to the front wall 16 has a guide 20 against which a filament 34 (as indicated in phantom) is slid as it is removed from a filament spool 33 (as indicated in phantom). The shoulder saddle 19 also contains a means for cutting 21 the filament. The means for cutting 21 the filament is positioned a distance from the guide 20 so that a length of the filament 34 is exposed providing an user easy access to the filament. It is preferable that the means for cutting 21 the filament is a metal detent commonly known in the art which permits cutting and capturing of the filament.

Figure 2:
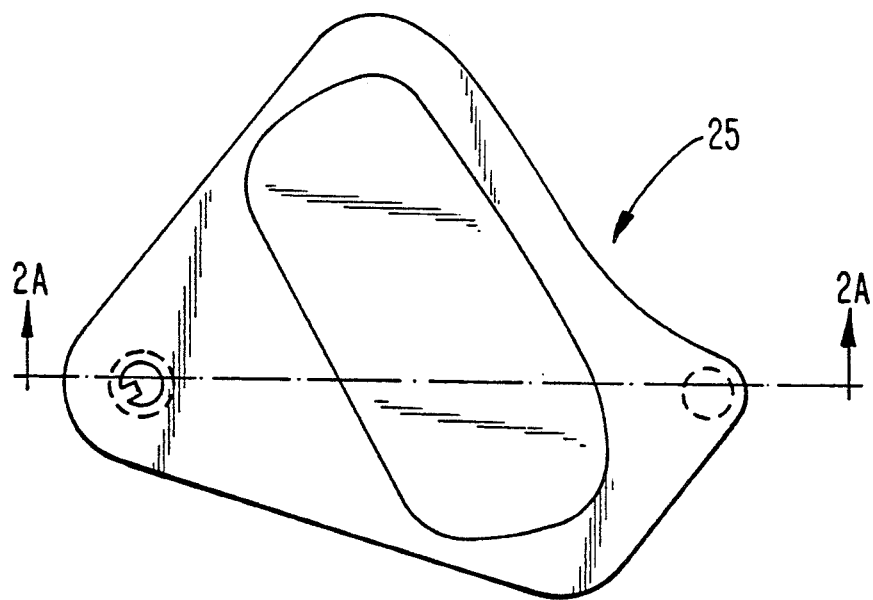
FIG. 2 is a planar view of a window assembly of the inventive dental floss assembly.

Referring to FIG. 2, a window assembly 25 is depicted in a planar view.

Figure 3:
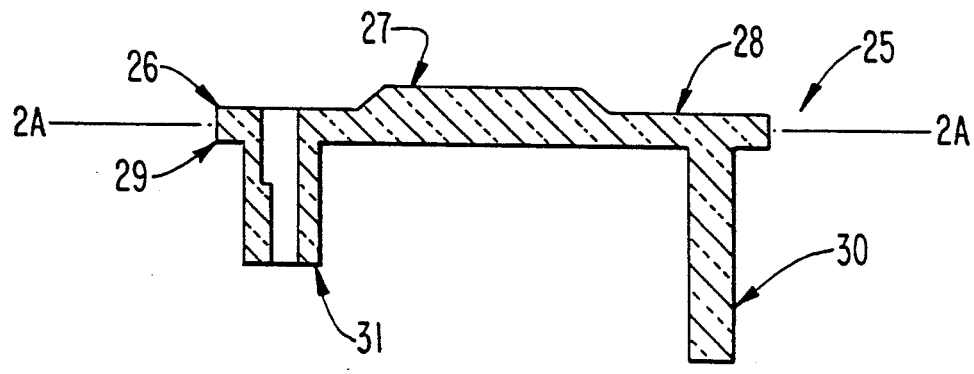
FIG. 3 is a cross sectional view of the window assembly of FIG. 2 taken along line 2A.

Referring to FIG. 3, a cross-section of the window assembly 25 of FIG. 2 taken along line 2A and having two faces is depicted. The window assembly is produced through molding of a transparent polymeric material. The transparent polymeric material should be accepted as safe for use in dental floss dispensers by the FDA. The preferred transparent polymeric material is polycarbonate which provides sufficient stiffness, strength and clarity to the window assembly. The transparent polymeric material may be tinted various colors thereby providing some indicia of any flavorings or additives that may be present in the filament.

Still referring to FIG. 3, the window assembly 25 has a first face 26 which comprises a transparent raised planar section 27 and surrounding the transparent raised planar section a peripheral flange 28. The window assembly 25 has a second face 29 on the other side which is arranged a column 30 in alignment with the peripheral flange 28. The column 30 is positioned away from the transparent raised planar section so as not to be visible by a user of the dispenser when the dispenser is in a closed position.

Still referring to FIG. 3, a hollow shaft 31 is depicted as having a circular outside diameter for receiving a filament spool and an having an axial bore with an internal profile complementary to the profile of the with a keyed profile. The hollow shaft 31 is positioned adjacent to the transparent raised planar section such that when a filament spool is placed around the circular outside of the hollow shaft 31, the filament spool is easily visible through the transparent raised planar section 27.

Figure 4:
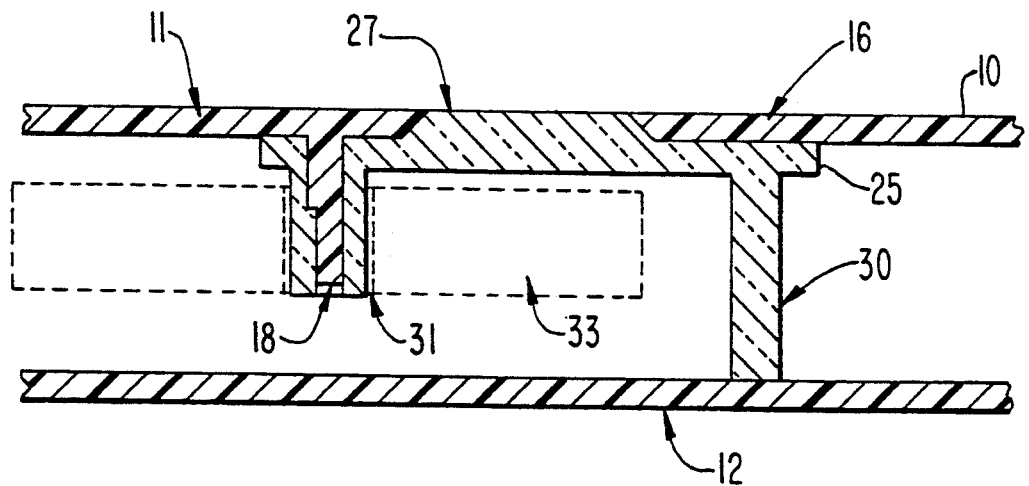
FIG. 4 is cross sectional view of the inventive dental floss dispenser depicting the window assembly engaged with the unitary plastic housing.

Referring to FIG. 4, the window assembly 25 is engaged with the molded unitary plastic housing 10 by positioning the transparent raised plastic housing with the opening in the front wall 11 of the unitary plastic housing and by meshing the axial bore of the hollow shaft 31 with the post having a keyed profile 18. The meshing of the hollow shaft 31 with the post 18 prevents the window assembly 25 from rotating about the post thereby assuring a secure fit. The column 30 engages the back section 12 of the molded unitary plastic enclosure, thereby allowing the window assembly greater resistance to forces applied to the transparent raised planar section in a normal direction.

Still referring to FIG. 4, the filament spool 33 (as indicated in phantom) is rotatably mounted on the shaft 31 and therefore positioned behind the transparent raised planar section 27 thereby permitting a user of the dispenser to determine the amount of filament remaining on the filament spool by viewing the filament spool through the transparent raised planar section.

Figure 5:
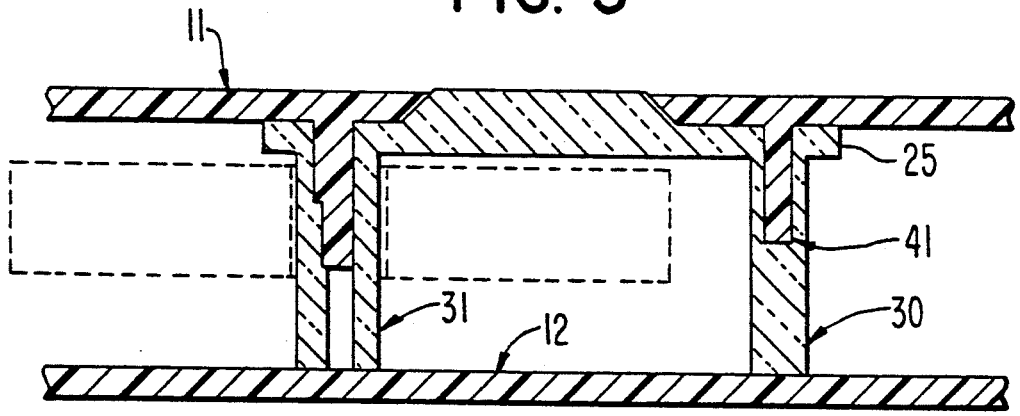
FIG. 5 is cross sectional view of another embodiment of the inventive dental floss dispenser depicting the window assembly engaged with the unitary plastic housing.

Referring to FIG. 5, an alternate embodiment of the inventive dental floss dispenser is depicted. A second post 41 is formed on the front wall 11 of the molded unitary plastic housing. A bore is located axially in the column 30 which is capable of receiving the second post therein. Engagement of the second post with the column permits a more secure engagement of the window assembly 25 with the molded unitary plastic housing. FIG. 5 also depicts an alternate embodiment of the inventive dental floss dispenser wherein the hollow shaft 31 is extended so that it contacts the back section 12 further strengthening the engagement of the window assembly 25 in the molded unitary plastic housing.

Figure 6:
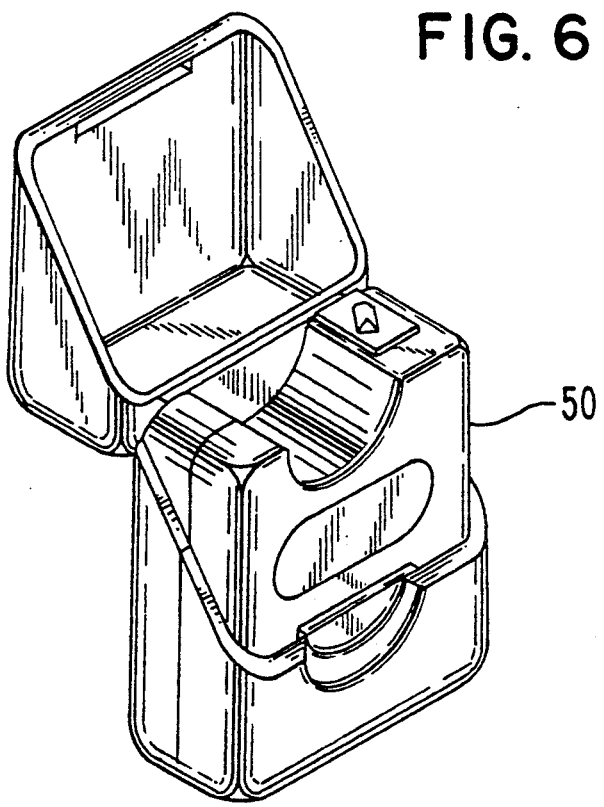
FIG. 6 is a perspective view of the inventive dental floss dispenser.

Referring to FIG. 6, a perspective view of the inventive dental floss dispenser 50 is depicted.

One of the advantages of the instant dental floss dispenser is the ability of the dispenser to be refilled be the user. The presence of two hinge means in the molded unitary plastic housing allows the user of the dispenser to fully open the dispenser thereby providing easy access to the shaft on which is rotatably mounted the filament spool. The presence of the transparent raised planar section allows the user of the dispenser to determine the amount of dental floss remaining on the filament spool without fully opening the dispenser.

While the invention has been disclosed herein in the detailed description, it will be clear to those skilled in the art that modifications or variations of such details can be made without deviating from the gist of this invention, and such modifications or variations are considered to be within the scope of the claims hereinbelow.

We claim:

1. A dental floss dispenser comprising:
   (a) a molded unitary plastic housing having a front section, a back section, a cover, a first hinge means interposed between the front section and the back section and a second hinge means interposed between the back section and the cover forming an enclosure for holding a filament spool, the front section being a front wall with an opening and a post having a keyed profile perpendicular and adjacent to the opening, and a shoulder saddle perpendicular to the front wall having a guide for sliding a filament from the enclosure and a means for cutting the filament; and (b) a window assembly engaged with the front section, the window assembly having two faces, the first face being arranged with a transparent raised planar section and a peripheral flange surrounding the transparent raised planar section and the second face being arranged with a column in alignment with the peripheral flange and projecting perpendicularly from the second face, and a hollow shaft, having a circular outside diameter for rotatably mounting the filament spool and an axial bore having an internal profile complementary to the post with a keyed profile, aligned with the peripheral flange and projecting perpendicularly from the second face, wherein the window assembly is engaged with the molded unitary plastic housing by positioning the transparent raised planar section within the opening in the front wall and by meshing the axial bore with the post having a keyed profile.

2. A dental floss dispenser according to claim 1 wherein the molded unitary plastic housing is of polypropylene.

3. A dental floss dispenser according to claim 1 wherein the window assembly having two faces is of polycarbonate.

4. A dental floss dispenser according to claim 3 wherein the window assembly having two faces is tinted.

5. A dental floss dispenser according to claim 1 further comprising a second post formed on the front wall of the molded unitary plastic housing and a bore located axially in the column which is capable of receiving the second post therein.

* * * * *